United States Patent [19]
Tallone

[11] Patent Number: 5,659,393
[45] Date of Patent: Aug. 19, 1997

[54] METHOD OF AND DEVICE FOR MEASURING THE REFRACTIVE INDEX OF WAFERS OF VITREOUS MATERIAL

[75] Inventor: Lugi Tallone, Paesana, Italy

[73] Assignee: Cselt- Centro Studi E Laboratori Telecomunicazioni S.p.A., Turin, Italy

[21] Appl. No.: 610,499

[22] Filed: Mar. 6, 1996

[51] Int. Cl.$^6$ .................................................. G01N 21/45
[52] U.S. Cl. ................................ 356/361; 356/128
[58] Field of Search ........................ 356/128, 355, 356/361

[56] References Cited

U.S. PATENT DOCUMENTS

| | | | |
|---|---|---|---|
| 4,553,841 | 11/1985 | Coppa et al. | 356/349 |
| 4,565,449 | 1/1986 | Grego | 356/361 |
| 5,074,666 | 12/1991 | Barnes et al. | 356/354 |
| 5,218,426 | 6/1993 | Hall et al. | |
| 5,305,077 | 4/1994 | Grego et al. | 356/346 |

FOREIGN PATENT DOCUMENTS

A-32 44 783  7/1984  Germany.

OTHER PUBLICATIONS

Review of Scientific Instruments, vol. 59, No. 4, Apr. 1988, pp. 652–653, Betzler K. et al, "Interferometic Measurement of Refractive Indices".

Applied Optics, vol. 25, No. 8, 15 Apr. 1986, pp. 1344–1349, Velsko S.P. et al, "Precise Measurements of Optical Dispersion Using A New Interferometric Technique".

Primary Examiner—Frank Gonzalez
Assistant Examiner—Zandra V. Smith
Attorney, Agent, or Firm—Herbert Dubno

[57] ABSTRACT

A light beam is sent onto a wafer, at different angles of incidence, thus giving rise to fluctuations in the transmittance of the wafer, as the angle of incidence varies, because of interference due to multiple reflections of the beam inside the wafer. The transmittance of the wafer is measured as the angle of incidence varies. The angular positions of transmittance maxima and minima are determined with respect to a maximum or minimum corresponding to normal incidence. The refractive index is obtained from these positions and from the number of maxima and minima in the different angles.

16 Claims, 4 Drawing Sheets

METHOD OF AND DEVICE FOR MEASURING THE REFRACTIVE INDEX OF WAFERS OF VITREOUS MATERIAL

FIELD OF THE INVENTION

My present invention relates to a method of measuring the refractive index and, more particularly to a method and a device for determining the refractive index of a wafer of vitreous material.

Preferably, but not exclusively, the invention is employed in measuring the refractive index in a limited area (about 1 $mm^2$) of a thin sample of an optical fiber preform of fluoride glass.

BACKGROUND OF THE INVENTION

It is well known that the refractive index of a body of a fluoride glass, such as an optical fiber preform, depends not only on the composition of the glass but also on its thermal history. In effect, during the casting and drawing processes stresses or inhomogeneities may arise which give rise to local fluctuations in the refractive index, which fluctuations must be detected and eliminated.

The conventional devices for measuring the refractive index of samples of transparent material, which are based on measuring the limit angle (for instance Pulfrich refractometers) require sending a grazing beam onto the sample and analyzing the beam refracted by the sample. These devices cannot be employed to measure directly the refractive index of the core and the cladding of an optical fiber, since the size of the sample is too small to obtain a significant amount of refracted light. Using a Pulfrich refractometer for measurements on a glass sample whose composition is analogous to that of the preform, on the other hand, does not allow taking into account the thermal history of the glass, and in particular the fact that the cooling conditions of a wafer are different from those of a cylindrical body like the preform.

European patent EP-B 0 085 978, describes a method of determining the refractive index, which method can also be employed in the case of small samples, such as those obtained by cutting an optical fiber preform. According to the known method, the sample is placed on a support which can be rotated. A light beam comprising two monochromatic radiations is sent towards the sample with a first angle of incidence and the two radiations are caused to interfere upon leaving the sample, thereby creating a first beat. Subsequently, the support is rotated, the beam is directed against on the sample with a second angle of incidence and the two radiations are again caused to interfere upon leaving the sample, thereby creating a second beat. The refractive index is obtained from the phase differences between the two beats and a reference beat obtained by making the two radiations of the beam interfere at the end of a path external to the sample.

However, radiations which pass through the sample inevitably undergo multiple reflections inside it, and these bring about interference phenomena which result in a phase error limiting the accuracy of the measurement to such an extent that it is no longer possible to appreciate said fluctuations in the refractive index. Moreover, the measurement is quite sensitive to thermal expansion and to electrical drift.

OBJECT OF THE INVENTION

A more detailed analysis of the disturbance caused by multiple reflections, carried out by the inventor in order to correct or in any case to take into account errors stemming from such disturbance, has yielded the surprising result that it is possible to exploit the disturbance itself to obtain an accurate measurement of the refractive index. The object of the invention is thus to provide a method and a device which exploit interference phenomena due to multiple reflections inside the sample.

SUMMARY OF THE INVENTION

According to the invention a method is provided in which a source generates a light beam which is sent towards the wafer at different angles of incidence and the intensity of a beam transmitted by the wafer is measured as the angle of incidence varies, and in which: the beam generated by the source is a coherent monochromatic beam whose coherence length exceeds the thickness of the wafer; said beam, before being sent towards the wafer, is transformed into a collimated beam with plane wave front, in order to give rise to fluctuations of the wafer transmittance as the angle of incidence varies, because of the interference due to multiple reflections of the beam inside the wafer; the values of the wafer transmittance are obtained from the measured values of the intensity; the angular positions of the transmittance maxima and minima are determined, within a preset range of angles of incidence, with respect to a maximum or a minimum corresponding to normal incidence, and the refractive index is obtained from these positions and from the number of maxima and minima in the different angles.

SPECIFIC DESCRIPTION

Figure 1:
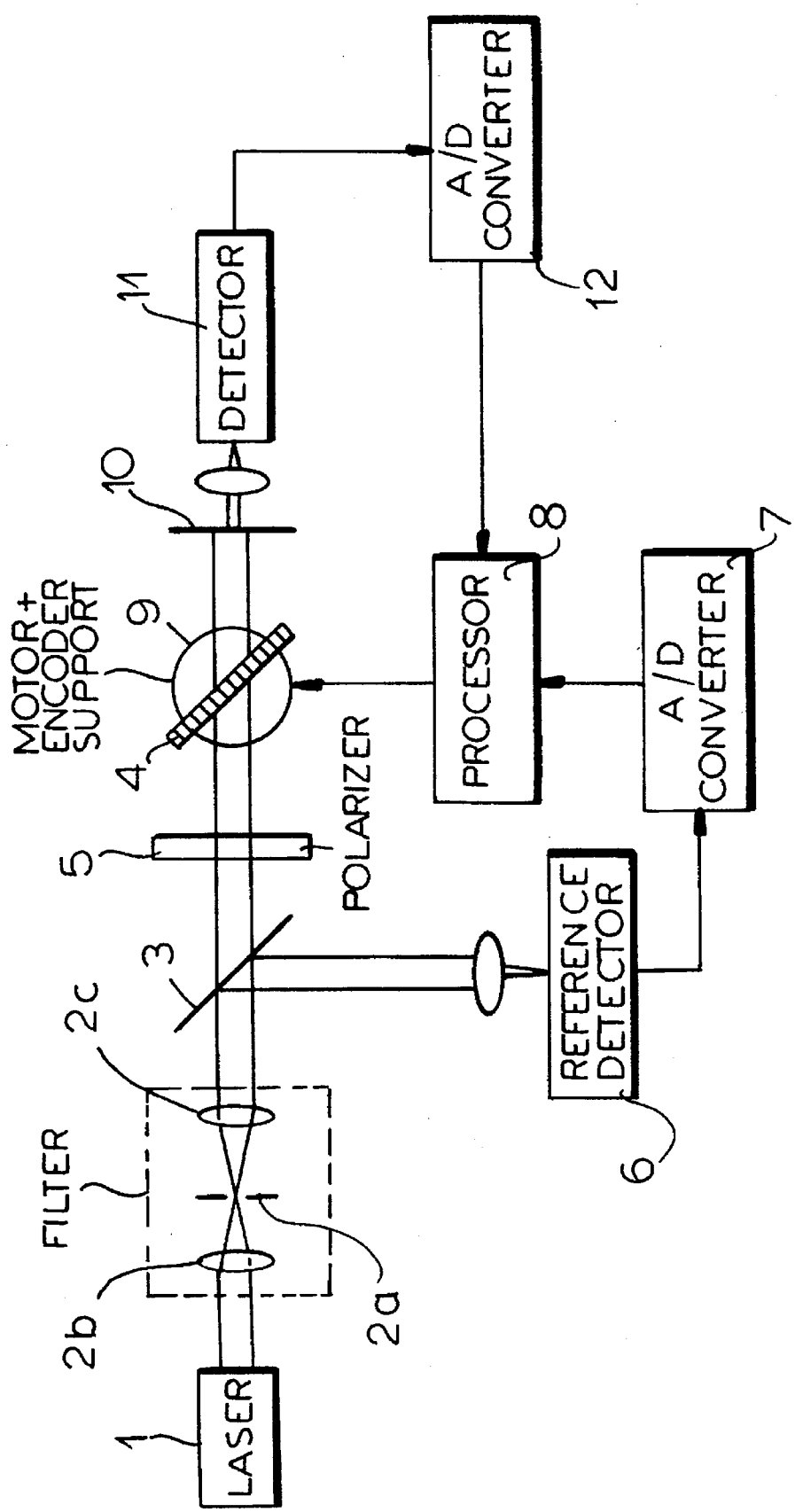
FIG. 1 is a schematic diagram of the device performing the method.

In FIG. 1, a source 1, e.g. a He-Ne laser, generates a beam of coherent monochromatic light. A spatial filter 2, comprising a pinhole diaphragm 2a placed between a first lens 2b, which focuses the beam emitted by the source onto the pinhole, and a second lens 2c, which collimates and expands the beam exiting the diaphragm, generates a beam with a planar wave front. The collimated beam is split into two fractions by means of a beam splitter 3. A first fraction is sent towards a sample 4, which is a wafer with plane and parallel faces whose thickness is smaller than the coherence length of source 1. This beam fraction passes through a polarizer 5 which orients the polarization plane of the beam fraction in such a way that the electrical field is parallel to the angle of incidence (S wave).

Inside the sample, the beam undergoes multiple reflections and, due to the characteristics of the beam, there are noticeable fluctuations in the transmittance of the sample as an effect of interference between the various reflected beams. These fluctuations are exploited to determine the refractive index. The particular choice of the polarization makes the measurements easy since the amplitude of the fluctuations is larger in the case of an S wave.

The second beam fraction is sent directly to a reference detector 6 whose output signals are provided to an analog-to-digital converter 7 connected to a processor 8.

Sample 4 is mounted on a motorised support 9 which can be rotated under the control of processor 8 to vary the angle of incidence of the beam on sample 4. The support is associated with an extremely accurate angular position detector, in particular, an encoder with the ability to provide the position of the support with an accuracy on the order of tenths of a second of a degree. For the sake of simplicity, in the drawing the motor and the encoder are incorporated in support 9. The beam exiting sample 4 passes through a movable diaphragm 10 which allows selection of the area of the sample on which the measurement is to be performed, and it is collected by a second detector 11 followed by an analog-to-digital converter 12 connected to processor 8.

Processor 8 receives, from converters 7 and 12, current or voltage values representing the intensities of the reference beam and of the beam transmitted by wafer 4 (which is proportional to transmittance) as the angle of incidence varies, and computes the ratio of said values, associating the values of that ratio to the angular position of the support. Note that the intensity of the transmitted beam only could be used for processing. However, as shall be better shown below, the actual value of transmittance is not of interest for the invention and using the ratio between the two intensities allows the effects of noise to be reduced. Assuming that support 9 is rotated in a range from +45° to −45° with respect to normal incidence, sufficient data for subsequent processing are obtained by rotating support 9 in steps of a few tens of seconds of a degree.

Figure 2:
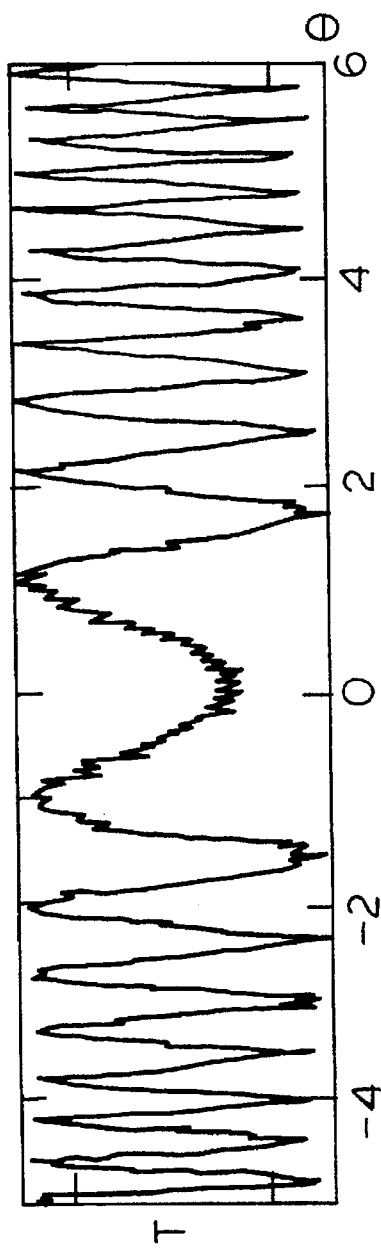
FIG. 2 is a diagram of the transmittance versus the angle of incidence, for a range of angles at the two sides of normal incidence.

FIG. 2 shows the transmittance versus the angle of incidence (in degrees) for a small range of angles on the two sides of normal incidence. The values of the ordinates are not indicated, since they depend on the measured quantity (intensity of the beam transmitted by the sample or ratio between transmitted beam and reference beam intensities). The Figure clearly depicts transmittance fluctuations due to interference phenomena caused by multiple reflections inside wafer 4, and shows that oscillation frequency increases as the angle of incidence increases. According to the invention, the refractive index is obtained by identifying the positions of maxima and minima of the curve in FIG. 2 with respect to the position of normal incidence (0 in the Figure) and the number of maxima and minima corresponding to the various rotation steps. This number, as will be shown below, can be expressed, for a given thickness of the sample and a given wavelength of the radiation used, as a function of refractive index and angle of incidence. The position of normal incidence is in turn accurately determined by identifying first the approximate point around which the curve is symmetrical, then two maxima or minima which are symmetrical with respect to that point and finally by choosing as angle 0 the intermediate value between the two considered maxima and minima. The operation is made easier by the oscillation frequency being relatively low near normal incidence.

For processing, the positions of transmittance maxima and minima are used in place of the actual values because the position is much less sensitive to errors due to drifts or to the state of cleanliness or finish of the faces of the sample. Greater processing complexity is counterbalanced by the improvement in accuracy.

Figure 3:
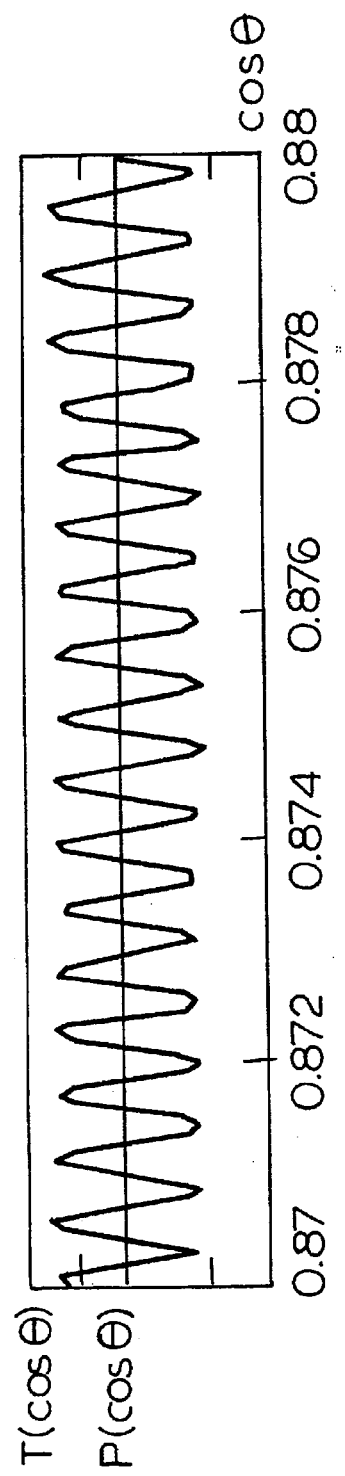
FIG. 3 are diagrams of the transmittance versus the cosine of the angle of incidence and of a second curve, used to determine the positions of transmittance maxima and minima.

To determine the positions of maxima and minima, intervals containing each one maximum and one minimum are looked for in the curve. For this purpose, a function $P(\theta)$ (for instance, a straight line or a curve corresponding to a second degree polynomial function with a very small coefficient of the second degree term) is determined from the data, which function intersects the peaks in FIG. 2 essentially at mid height, and the values of $\theta$ corresponding to the intersections between the two curves are identified. Operations are simplified if both T and P are expressed as a function of $\cos\theta$, since peaks in function $T(\cos\theta)$ are essentially equally spaced, as FIG. 3 shows. For the sake of simplicity, a function of the type $P(\cos\theta)$=constant was considered for curve P in the drawing. Intersection points between P and T are those for which, in the points of the two curves P, T corresponding to two successive positions of sample 4, relation $$(T_i - P_i) \cdot (T_{i-1} - P_{i-1}) \quad (1)$$

applies, and moreover the distance between the previous point in which relation (1) has been met and the current point exceeds a given value (e.g. the distance between successive peaks) so as to eliminate spurious intersection points due to noise. Once the intervals have been determined, it is sufficient to approximate the experimental curve in each interval with a polynomial of at least the $3^{rd}$ degree and to determine analytically the maximum and minimum thereof. The refractive index is then obtained from the angular positions $\theta_K$ of the maxima and minima of T and from the overall number $V_K$ of the maxima and minima present in the interval $0-\theta_K$.

The following description provides a brief outline of the theory on which the method according to the invention is based.

Considering sample 5 as a multi-layer, transmittance T can be expressed as a function of angle of incidence $\theta$, wavelength $\lambda$ of the incident radiation, refractive index n and thickness d according to the following relation:

$$T(\theta, n, d, \lambda) = \frac{1}{C(\theta,n) + D(\theta,n) \cdot \cos\left[\frac{4\pi}{\lambda} \cdot d \cdot n \cdot N(\theta,n)\right]} \quad (2)$$

where $$N(\theta,n) = \sqrt{1 - \text{sen}^2\theta/n^2} \quad (3)$$

$$C(\theta,n) = \frac{1}{4} \cdot \left[\frac{1}{2} \cdot \left(\frac{\cos\theta}{n \cdot N(\theta,n)} + 1\right) + \frac{n \cdot N(\theta,n)}{2\cos\theta} \cdot \left(\frac{\cos\theta}{n \cdot N(\theta,n)} + 1\right)\right]^2 \quad (4)$$

$$D(\theta,n) = \frac{1}{4} \cdot \left\{1 - \frac{1}{2} \cdot \left(\frac{\cos\theta}{n \cdot N(\theta,n)} + 1\right) - \frac{n \cdot N(\theta,n)}{2\cos\theta} \cdot \left[1 - \frac{1}{2} \cdot \left(\frac{\cos\theta}{n \cdot N(\theta,n)} + 1\right)\right]^2\right\} \quad (5)$$

The relations above are obtained by applying the principles described for example in "Theory and calculations of optical thin films", by P. H. Berning, Physics of thin films, Vol. 1 pages 69 and fol. To identify the positions of the maxima and minima of T as a function of $\theta$ it will be enough to compute the derivative of T with respect to $\theta$ and to set it to 0. The result is a relation of the type:

$$\sin\left\{4\cdot\pi\cdot d\cdot n\cdot N(\theta,n)+\text{arctg}\left[\frac{\frac{\partial D(\theta,n)}{\partial\theta}}{-4\cdot\pi\cdot d\cdot n\cdot\frac{\partial N(\theta,n)}{\partial\theta}}\right]\right\} = \quad (6)$$

$$= \frac{-\frac{\partial C(\theta,n)}{\partial\theta}}{\sqrt{\left(\frac{\partial D(\theta,n)}{\partial\theta}\right)^2+\left[4\cdot\pi\cdot d\cdot n\cdot\frac{\partial N(\theta,n)}{\partial\theta}\right]^2}}$$

It can be verified that, for refractive index values typical of vitreous materials (in particular <2), thicknesses of a few millimeters and wavelengths in the visible spectrum, in the range of angles under consideration the second member of relation (6) is very small (<0.001) and therefore the sine of the first member can be considered equal to its argument. Therefore, relation (6) is equal to 0 when the argument of the sine is equal to $m\pi$, i.e. when $$m \cong 4\cdot d\cdot n\cdot N(\theta,n)+\frac{1}{\pi}\text{arctg}\left[\frac{\frac{\partial D(\theta,n)}{\partial\theta}}{-4\cdot\pi\cdot d\cdot n\cdot\frac{\partial N(\theta,n)}{\partial\theta}}\right] \quad (7)$$

Now, let us consider the function:

$$F(\theta,n,d,\lambda) = \frac{4}{\lambda}\cdot d\cdot n\cdot N(0,n) + \quad (8)$$

$$\frac{1}{\pi}\text{arctg}\left[\frac{\frac{\partial D(0,n)}{\partial\theta}}{-4\cdot\pi\cdot d\cdot n\cdot\frac{\partial N(0,n)}{\partial\theta}}\right] -$$

$$-\frac{4}{\lambda}\cdot d\cdot n\cdot N(\theta,n) - \frac{1}{\pi}\text{arctg}\left[\frac{\frac{\partial D(\theta,n)}{\partial\theta}}{-4\cdot\pi\cdot d\cdot n\cdot\frac{\partial N(\theta,n)}{\partial\theta}}\right]$$

Figure 4:
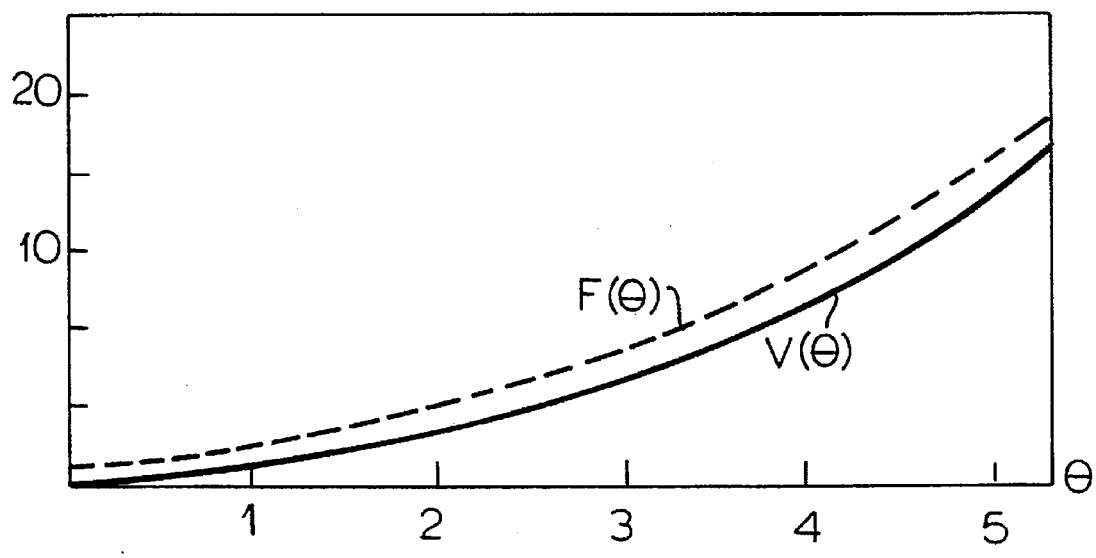
FIG. 4 is a diagram plotting the number of transmittance maxima and minima determined using the curves in FIG. 3, versus the angle of incidence, as well as the trend of a theoretical function linked to that number.

This function is equal to 0 for θ=0 and can be interpreted, when it has an integer value, as the overall number of maxima and minima of T. Moreover, its trend is very similar to that of the curve obtained by plotting number V of maxima and minima of T, determined in the way described above, versus θ. This similarity can clearly be seen in FIG. 4, where the solid line corresponds to the aforesaid plot and the dashed line to curve (8). The trend of curve (8) varies abruptly even for small variations of n: however, if for each value of n one of the two curves is translated vertically so that it intersects the other in one point, the difference between the two curves, in the range of angles under consideration, is negligible (<10⁻⁹). The value of n that minimizes the differences between curve (8) and the experimental data in the range of angles under consideration shall be the value of the refractive index of the sample.

To obtain satisfactory results it is necessary to take some measures, which allow minimising the effects of error due to the inaccuracy in the knowledge of thickness d and taking into account only the shape of the curve F and not the position.

To take into account the shape of the curve, one can consider the difference between the value of F and the experimental value for a first angle $\theta_R$ which can be the angle of normal incidence or the angle corresponding to one of the first peaks of the curve in FIG. 2. The effect of thickness d can be minimized by normalizing both V and function F (already corrected to take into account the shape difference) with respect to the value corresponding to a second angle $\theta_F$, for example an angle near the last peak. In practice, denoting by $V_K$, $V_R$, $V_F$ the number of maxima and minima in correspondence with a generic angle $\theta_K$ and respectively with angles $\theta_R$ and $\theta_F$, and by N the total number of maxima and minima determined experimentally, the refractive index can be determined by minimizing function $$M(n,\lambda,d) = \sum_{K=1}^{N}\left[\frac{V_K-V_R}{V_F-V_R} - \frac{F(\theta_K,n,d,\lambda)-F(\theta_R,n,d,\lambda)}{F(\theta_F,n,d,\lambda)-F(\theta_R,n,d,\lambda)}\right]^2 \quad (9)$$

The accuracy in measuring n can be further improved by using in relation (6), instead of $V_R$, $V_F$, values obtained through interpolation, with a second degree curve, of a preset number of previous and subsequent values, for example 50.

Figure 5:
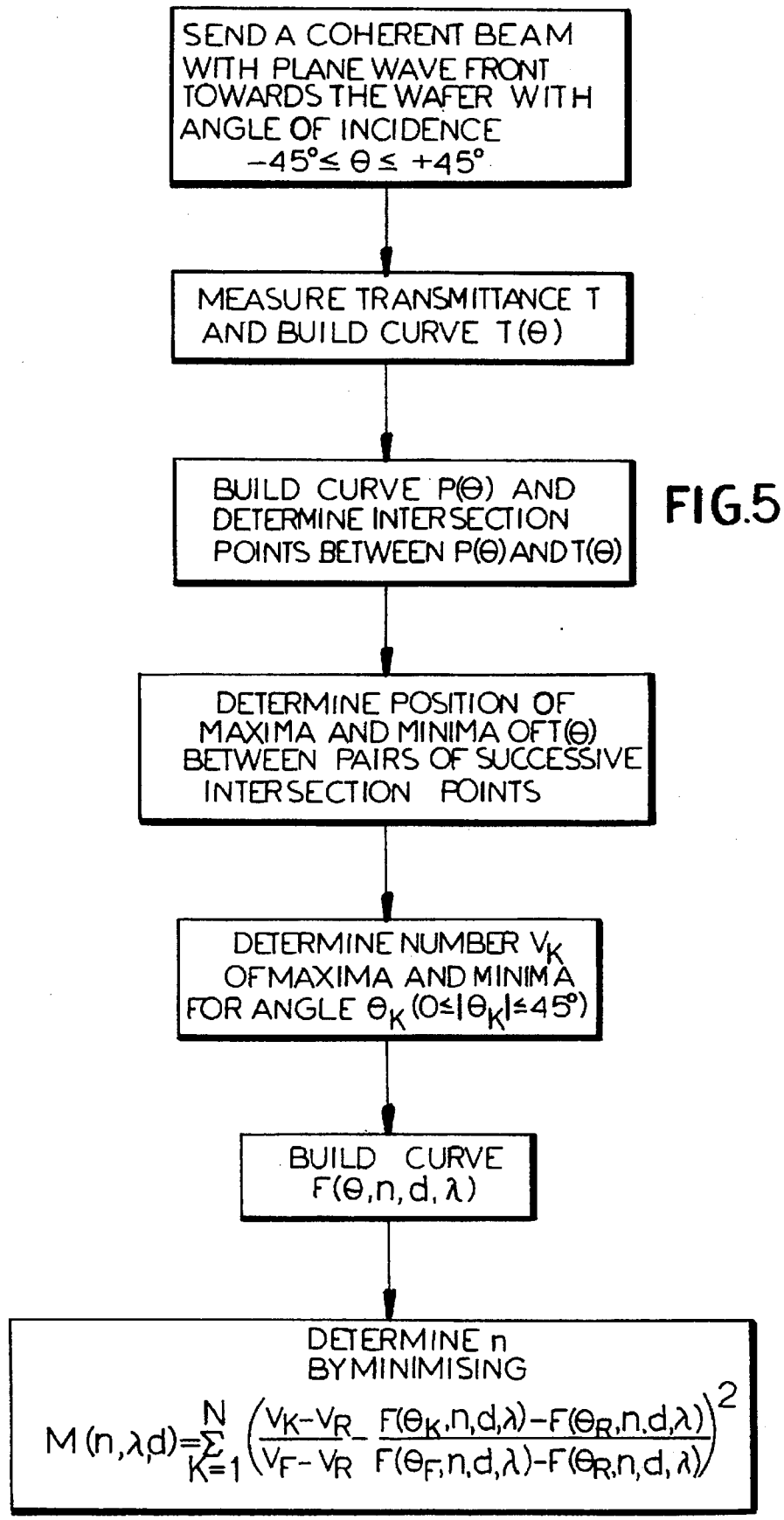
FIG. 5 is a flow chart illustrating the operations of the method according to the invention.

The operations described above are also reported in the flow chart in FIG. 5.

The system just described does not require the creation of a beat between beams following different paths, so clearly it is immune to disturbances, such as thermal expansion in the components of the device, which cause variations in the optical path (aside from possible expansions of the wafer, which in any case are negligible with respect to those of the external components). Exploiting the number of transmittance maxima and minima and not their values, moreover, renders the system immune to electrical drifts.

I claim:

1. A method of determining the refractive index of a wafer of vitreous material having plane parallel faces, comprising the steps of:
   (a) generating a beam of light and sending said beam towards the wafer at different angles of incidence and measuring the intensity of a beam transmitted by the wafer as the angle of incidence varies, the beam being a coherent monochromatic beam whose coherence length exceeds the thickness of the wafer;
   (b) transforming said beam, before the beam is sent towards the wafer, into a collimated beam with a planar wave front, in order to give rise to fluctuations in the transmittance of the wafer as the angle of incidence varies, because of interference due to multiple reflections of the beam inside the wafer;
   (c) obtaining values of the transmittance of the wafer from respective measured intensity values; and
   (d) determining the angular positions of transmittance maxima and minima within a present range of angles of incidence, with respect to a value corresponding to the normal incidence, and obtaining the refractive index from said positions and from the number of maxima and minima in the different angles.

2. The method defined in claim 1 wherein the collimated beam is polarized in such a way that the electric field is parallel to the plane of incidence on the wafer.

3. The method defined in claim 1 wherein the beam transmitted by the wafer is caused to pass through a diaphragm to select a limited area of the wafer.

4. The method defined in claim 1 wherein the values of the transmittance of the wafer are obtained from a ratio between the intensity of a first fraction of the collimated beam, which is sent towards the wafer, and the intensity of a second fraction of the beam, which constitutes a reference beam.

5. The method defined in claim 1 wherein, to determine the positions of transmittance maxima and minima, a first curve representative of the transmittance as a function of the angle of incidence, and a second curve representative of an average value of the transmittance as a function of the angle of incidence, are constructed starting from the measured transmittance values; the intersection points between the two curves are determined such that the distance between two successive intersection points be larger than a preset fraction of the period of the transmittance fluctuations in correspondence with the intersection points, so as to subdivide the first curve into intervals, each including a transmittance maximum and a minimum; the first curve is approximated in each of said intervals with a polynomial function, of suitable degree, of the angle of incidence; and the positions of the maximum and minimum points of this polynomial function determined analytically.

6. The method defined in claim 5 wherein the refractive index is obtained by counting, for each angle of incidence, the number of transmittance maxima and minima as an experimental value of the number of maxima and minima obtained by means of said subdivision of the first curve and occurring between the angle off normal incidence and the angle under consideration, and by minimizing the differences between said experimental values and corresponding values of an analytical function of the angle of incidence, the refractive index, the wafer thickness and the beam wavelength, whose value is 0 in correspondence with the normal incidence and in which integer values represent each the sum of transmittance maxima and minima occurring between normal incidence and the angle corresponding with the said integer value.

7. The method defined in claim 6 wherein, for minimization, for each angle of incidence, a difference between the experimental value associated with that angle and the experimental value associated with a first reference angle, and a difference between the values assumed by the analytical function in the angle of incidence under consideration and in the reference angle are computed, and said differences are normalized with respect to the values they assume when the angle of incidence is equal to a second reference angle.

8. The method defined in claim 7 wherein, the first reference angle is the angle of normal incidence or an angle corresponding to one of the transmittance maxima or minima near the maximum or minimum associated with normal incidence, and the second reference angle is the extreme angle of said range or an angle near that extreme.

9. The method defined in claim 7 wherein the experimental values of the number of maxima and minima corresponding with the reference angles are obtained through interpolation, from a preset number of previous and subsequent values.

10. The method defined in claim 7 wherein said wafer is a fluoride glass wafer obtained from an optical fiber preform.

11. A device for the determination of the refractive index of a wafer of vitreous material and having plane parallel faces, the device comprising:

a source of a light beam;

means for sending at least a fraction of the beam towards the wafer;

a support for the wafer provided with means for causing rotation of the wafer to vary an angle of incidence of the beam on the wafer and with means for detecting an angular position of the support;

means receiving the beam exiting the wafer for providing signals representing the intensity of the beam exiting the wafer; and a processing system controlling the movements of the support and processing the intensity signals as required to obtain the refractive index, the source being a source of a coherent monochromatic beam whose coherence length exceeds the thickness of the wafer;

the means for sending at least a fraction of the beam towards wafer comprising a spatial filter placed between the source and the wafer and arranged to transform the beam emitted by the source into a collimated beam with a planar wave front, in order to give rise to fluctuations of the transmittance of the wafer as the angle of incidence varies, because of interference due to multiple reflections of the beam inside the wafer; and the processing system being arranged to obtain, from the intensity signals, values of the transmittance of the wafer as the angle of incidence of the beam varies, to determine the positions of transmittance maxima and minima with respect to a value corresponding to normal incidence, and to obtain the refractive index from said positions and from the number of maxima and minima.

12. The device defined in claim 11 wherein the means sending at least a fraction of the beam emitted by the source towards the wafer also comprises a polarizer placed between the spatial filter and the wafer, to polarize at least a fraction of the collimated beam so that the electric field is parallel to the incidence plane on the wafer.

13. The device defined in claim 12 wherein the means sending at least a fraction of the beam emitted by the source towards the wafer comprises a beam splitter downstream of the spatial filter and which divides the collimated beam into a first fraction which is sent towards the wafer through the polarizer, and into a second fraction, which constitutes a reference beam;

means being provided for receiving the reference beam and for providing signals representing the intensity of such beam;

the processing system being arranged to process wafer transmittance values obtained from the ratio between the intensities of the two beam fractions.

14. The device defined in claim 11 wherein a movable diaphragm is arranged between the wafer and the means collecting the transmitted beam to select a beam portion exiting a limited area of the wafer.

15. The device defined in claim 11 wherein, to obtain the refractive index, the processing system is arranged to perform the following processing functions:

determining, starting from the transmittance values obtained, a first curve, representative of the transmittance as a function of the angle of incidence, and a second curve, representative of an average value of the transmittance as a function of the angle of incidence;

determining the intersection point between the two curves, such that the distance between two successive points exceeds a preset fraction of the period of the transmittance fluctuations in correspondence with such points, so as to subdivide the first curve into intervals, each including a maximum and a minimum of the transmittance;

approximating the experimental curve in each interval with a polynomial function of the angle of incidence;

analytically determining the maximum and the minimum points of said polynomial function; and counting, for each angle of incidence, the number of transmittance maxima and minima forming experimental values of the number of maxima and minima obtained by said subdivision of the first curve and occurring between the angle of normal incidence and the angle under consideration, and minimizing the differences between the experimental values and the corresponding values assumed by an analytical function of the angle of incidence, the refractive index, the wafer thickness and the beam wavelength, whose value is 0 in correspondence with normal incidence and whose integer values represent each the sum of the transmittance maxima and minima occurring between normal incidence and the angle corresponding to that integer value.

16. The device defined in claim 11 wherein said wafer, is a fluoride glass wafer obtained from an optical fiber preform.

* * * * *